United States Patent
Beyer et al.

(10) Patent No.: US 11,738,501 B2
(45) Date of Patent: Aug. 29, 2023

(54) SYSTEM FOR ADDITIVE MANUFACTURING OF THREE-DIMENSIONAL STRUCTURES AND METHOD FOR SAME

(71) Applicant: ASPECT BIOSYSTEMS LTD., Vancouver (CA)

(72) Inventors: Simon Travis Beyer, Richmond (CA); Konrad Walus, Vancouver (CA); Tamer Mohamed, Richmond (CA); Anas Amjad Mohammad Bsoul, Vancouver (CA)

(73) Assignee: ASPECT BIOSYSTEMS LTD.

( * ) Notice: Subject to any disclaimer, the term of this patent is extended or adjusted under 35 U.S.C. 154(b) by 0 days.

(21) Appl. No.: 17/359,266

(22) Filed: Jun. 25, 2021

(65) Prior Publication Data

US 2021/0317404 A1 Oct. 14, 2021

Related U.S. Application Data

(62) Division of application No. 14/898,036, filed as application No. PCT/CA2014/050556 on Jun. 13, 2014, now Pat. No. 11,046,930.

(Continued)

(51) Int. Cl.
*B29C 64/106* (2017.01)
*B29C 64/209* (2017.01)
(Continued)

(52) U.S. Cl.
CPC .......... *B29C 64/106* (2017.08); *B29C 64/209* (2017.08); *B29C 70/00* (2013.01);
(Continued)

(58) Field of Classification Search
CPC ..... B29C 64/112; B29C 64/106; B29C 64/20; B29C 64/209; B33Y 30/00; C12M 21/08;
(Continued)

(56) References Cited

U.S. PATENT DOCUMENTS 7,033,603 B2 4/2006 Nelson et al.
7,625,198 B2 12/2009 Lipson et al.
(Continued)

FOREIGN PATENT DOCUMENTS

EP 605767 A1 4/1994
EP 1790861 A1 5/2007
(Continued)

OTHER PUBLICATIONS

Kang et al_Nature Materials_vol 10_Nov. 2011_Supplementary Information (Year: 2011).*

(Continued)

*Primary Examiner* — Yunju Kim
(74) *Attorney, Agent, or Firm* — Todd Lorenz

(57) ABSTRACT

A system and method for additive manufacturing of three-dimensional structures, including three-dimensional cellular structures, are provided. The system comprises at least one print head for receiving and dispensing materials, the materials comprising a sheath fluid and a hydrogel, the print head comprising an orifice for dispensing the materials, microfluidic channels for receiving and directing the materials, fluidic switches corresponding to one of the microfluidic channels in the print head and configured to allow or disallow fluid flow in the microfluidic channels; a receiving surface for receiving a first layer of the materials dispensed from the orifice; a positioning unit for positioning the orifice of the print head in three dimensional space; and a dispensing means for dispensing the materials from the orifice of the print head.

22 Claims, 10 Drawing Sheets

Related U.S. Application Data

(60) Provisional application No. 61/834,420, filed on Jun. 13, 2013.

(51) Int. Cl.

| | | |
|---|---|---|
| *B29C 70/00* | (2006.01) | |
| *B33Y 10/00* | (2015.01) | |
| *B33Y 30/00* | (2015.01) | |
| *C12M 3/00* | (2006.01) | |
| *C12M 3/06* | (2006.01) | |
| *C12M 1/26* | (2006.01) | |
| *C12N 5/00* | (2006.01) | |
| *C12N 11/04* | (2006.01) | |
| *B33Y 50/02* | (2015.01) | |
| *B29K 105/00* | (2006.01) | |

(52) U.S. Cl.
CPC ............. *B33Y 10/00* (2014.12); *B33Y 30/00* (2014.12); *C12M 21/08* (2013.01); *C12M 23/16* (2013.01); *C12M 33/00* (2013.01); *C12N 5/0068* (2013.01); *C12N 11/04* (2013.01); *B29K 2105/0058* (2013.01); *B29K 2105/0061* (2013.01); *B33Y 50/02* (2014.12); *C12N 2513/00* (2013.01); *C12N 2533/30* (2013.01)

(58) Field of Classification Search
CPC ..... C12M 23/16; C12M 33/00; C12N 5/0062; C12N 5/0068; C12N 2513/00; C08J 3/075
USPC ....................................................... 425/215
See application file for complete search history.

(56) References Cited

U.S. PATENT DOCUMENTS

| | | |
|---|---|---|
| 7,939,003 B2 | 5/2011 | Bonassar et al. |
| 8,047,235 B2 | 11/2011 | Lyons et al. |
| 8,636,938 B2 | 1/2014 | Bonassar et al. |
| 8,785,195 B2 | 6/2014 | Takeuchi et al. |
| 8,877,112 B2 | 11/2014 | Bonassar et al. |
| 9,242,031 B2 | 1/2016 | Bonassar et al. |
| 9,958,088 B2 | 5/2018 | Lee et al. |
| 2006/0105011 A1 | 5/2006 | Sun et al. |
| 2008/0070304 A1 | 3/2008 | Forgacs et al. |
| 2008/0206383 A1 | 8/2008 | Hull |
| 2010/0060875 A1 | 3/2010 | Kwon et al. |
| 2011/0006453 A1 | 1/2011 | Ying et al. |
| 2011/0136162 A1 | 6/2011 | Sun et al. |
| 2011/0190904 A1 | 8/2011 | Lechmann |
| 2011/0193259 A1 | 8/2011 | Howell et al. |
| 2011/0293712 A1 | 12/2011 | Kurt et al. |
| 2012/0089238 A1 | 4/2012 | Kang et al. |
| 2012/0322154 A1 | 12/2012 | Park et al. |
| 2014/0012407 A1 | 1/2014 | Murphy et al. |
| 2014/0232035 A1 | 8/2014 | Bheda |
| 2014/0328963 A1 | 11/2014 | Mark |
| 2016/0136895 A1 | 5/2016 | Beyer et al. |

FOREIGN PATENT DOCUMENTS

| | | |
|---|---|---|
| EP | 2489779 A1 | 8/2012 |
| EP | 3670155 A1 | 6/2020 |
| JP | 2008-017798 A | 1/2008 |
| NO | 2012075527 A1 | 6/2012 |
| WO | WO 2009/060202 A1 | 5/2009 |
| WO | WO 2011140627 A1 | 11/2011 |
| WO | WO 2012009363 A1 | 1/2012 |
| WO | WO 2012054195 A1 | 4/2012 |
| WO | WO 2013158508 A1 | 10/2013 |
| WO | WO 2014197999 A1 | 12/2014 |
| WO | WO 2015066705 A1 | 5/2015 |

OTHER PUBLICATIONS

Beyer, et al. "3D Alginate Constructs for Tissue Engineering Printed Using a Coaxial Flow Focusing Microfluidic Device," Transducers, Barcelona, Spain, Jun. 16-20, 2013, Downloaded from http://ieeexplore.ieee.org/xpls/icp.jsp? amumber=6626990.

Choi et al., "Microfluidic fabrication of complex-shaped microfibers by liquid template-aided multiphase microflow," Lab Chip, vol. 11, pp. 1477-1483 (2011).

Ghorbanian, "Microfluidic probe for direct write of soft cell scaffolds," M.Eng. Thesis. McGill University: Canada (2010).

Hu et al. "Hydrodynamic spinning of hydrogel fibers," Biomaterials, 31:863-869 (2010).

Hwang et al., "Microfluidic Chip-Based Fabriaction of PLGA Microfiber Scaffolds for Tissue Engineering", Langmuir, vol. 24, pp. 6845-6851 (2008).

Kang et al. "Novel PDMS cylindrical channels that generate coaxial flow, and application to fabrication of nicrofibers and particles", Lab on a Chip, 10:1856-1861 (2010).

Kang et al. "Digitally tunable physicochemical coding of material composition and topography in continuous nicrofibers", Nature Materials, 10:877-883 (2011).

Kang et al., "Microfluidic on the Fly Fabrication of Microstructures for Biomedical Applications", Microfluidic Technolgies fo Human Health, Chapter 12, pp. 293-309 (2012).

Khalil et al., "Bioprinting endothelial cells with alginate for 3D tissue constructs," Journal of Biomechanical Engineering, 131:111002-1-111002-8 (2009).

Kim et al., "Fabrication of cell-encapsulated alginate microfiber scaffold using microfluidic channel", Journal of Manufacturing Science and Engineering, 130:021016-1-021016-6 (2008).

Moon et al., "Tissue Engineering Part C: Methods: Layer by Layer Three-dimensional Tissue Epitaxy by Cell-Laden Hydrogel Droplets," 16(1):157-166 (2010).

Nishiyama et al., "Development of a Three-Dimensional Bioprinter: Construction of Cell Supporting Structures Using Aydrogel and Sate-of-the-Art Inkjet Technology," Journal of Biomedical Engineering, 131(3):0156-0161 (2009).

Onoe et al., "Core-shell gel wires for the construction of large area heterogeneous structures with biomaterials," EEE MEMS Conference, pp. 248-251 (2010).

Onoe et al., "Metre-long cell-laden microfibres exhibit tissue morphologies and functions," Nature Materials, vol. 12, pp. 584-590 (2013).

Shin et al.,"On the fly" continuous generation of alginate fibers using a microfluidic device, Langmuir, 23:9104-9108 (2007).

Yamada et al., "Microfluidic synthesis of chemically and physically anisotropic hydrogel microfibers for guided cell growth and networking", Soft Matter, vol. 8, No. 11, pp. 3122-3130 (2012).

Yu, Yin and Ozbolat, Ibrahim, "Cell Viability Characterization of Bioprintable Blood-vessel-like Cellular Channels towards 3D Organ Fabrication", Proceedings of the 2013 Indistrial and Systems Enineering Research Conference, A Krishnamurth and W.K.V. Chan, eds. (2013).

Bosnakovski et al., "Chondrogenic Differentiation of Bovine Bone Marrow Mesenchymal Stem Cells (MSCs) in Different Hydrogels: Influence of Collagen Type II Extracellular Matrix on MSC Chondrogensis", Wiley Periodicals Inc. (Feb. 9, 2006).

Hong, J.S, "Spherical and cylindrical microencapsulation of living cells using microfluidic devices", Korea-Austria Rheology Journal, vol. 19, No. 3, pp. 157-164 (2007).

Henmi et al., "Development of an Effective Three Dimensional Fabrication Technique Using Inkjet Technology for Tissue Model Samples", Proc. 6th World Congress on Alternatives & Animal Use in the Life Sciences Aug. 21-25, 2007, AATEX 14:689-692 (2008).

Jain et al., "Retrievable, Replaceable, Macroencapsulated Pancreatic Islet Xenografts", Transplantation, vol. 59, No. 3, pp. 319-324 (1995).

Lee et al., "Synthesis of Cell-Laden Hollow Fibers Using Microfluidic Chips and Microvascularized Tissue-Engineering Applications", Wiley InterScience 5(11):1264-68 (2009).

(56) References Cited

OTHER PUBLICATIONS

Prevost et al., "Application of AN69® Hydrogel to Islet Encapsulation: Evaluation in Streptozotocin-induced Diabetic Rat Model", Annals New York Academy of Sciences, vol. 832, Issue 1, pp. 344-349 (Dec. 17, 2006).

Takei et al., "Development of mammalian cell-enclosing calcium-alginate hydrogel fibers in a co-flowing stream", Biotechnol. J. vol. 1, pp. 1014-1017 (2006).

Takei et al., "Novel Technique to Control Inner & Outer Diameter of Calcium Alginate Hydrogel Hollow Microfibers & Immobilization of Mammalian Cells", Biochem. Eng. J. 49:143-147 (2010).

Tanaka et al. "A Novel Immobilization Method for Prevention of Cell Leakage from the Gel Matrix", J. Fermentation & BioEng. vol. 68:216-219 (1989).

Then et al., "A New Technique for Mechanically Characterizing Hydrogels for Tissue Engineering Cornea", Investigative Ophthalmology & Visual Science 46:2185 (2005).

Yu et al., "Encapsulation of rat hepatocyte spheroids for the development of artificial liver", Biotech. Tech. vol. 13, pp. 609-614 (1999).

\* cited by examiner

SYSTEM FOR ADDITIVE MANUFACTURING OF THREE-DIMENSIONAL STRUCTURES AND METHOD FOR SAME

CROSS REFERENCE TO PRIOR APPLICATIONS

This application claims priority under the Paris Convention from U.S. Application No. 61/834,420, filed on Jun. 13, 2013, the entire contents of which are incorporated herein by reference.

FIELD OF THE INVENTION

The present invention relates generally to three-dimensional (3D) printing and generation of three-dimensional biological structures from digital files. Specifically, the invention relates to a system, apparatus and method for fabricating 3D cell-laden hydrogel structures.

BACKGROUND OF THE INVENTION 3D printing, a form of additive manufacturing (AM), is a process for creating three-dimensional objects directly from digital files. Software is used to slice a computer aided design (CAD) model or a 3D scan of an object into a multitude of thin cross-sectional layers. This collection of layers is sent to the AM system where the system builds the three-dimensional object layer by layer. Each layer is deposited on top of the previous layer until the object has been fully constructed. Support material can be used to support overhanging and complex features of the object. Various AM processes exist that can build parts in plastic, metal, ceramic and/or biological materials.

Additive manufacturing could have applications in biological systems. For example, until recently, most cell culture studies were performed on 2-dimensional (2D) surfaces, such as micro-well plates and Petri dishes. However, 2D culture systems do not mimic the 3D environment in which cells exist in vivo. Researchers have found that 3D cell cultures behave more like natural biological tissue than 2D cell cultures at least in part because the 3D arrangement of cells in natural tissue influences cell-cell interactions, which in turn influences cell growth and physiology.

Additive manufacturing devices and systems for fabricating cellular constructs are known. For example, known fused fiber deposition techniques have been applied to biological materials. In fused fiber deposition, high viscosity liquids are dispensed from a relatively narrow orifice and then rapidly solidified by a variety of means. Biocompatible plastics, thermal gelling hydrogels, UV-cross-linkable polymers and high concentration alginates have been used as scaffolds for 3D cellular structures, wherein cells are added to the scaffold after it has solidified. A draw back to these techniques is that they require cells to be added to the scaffold after printing, making it difficult to control cell placement. Further, the composition of the scaffold substrates may not be appropriate for facilitating cell proliferation and growth.

Systems for printing 3D structures that comprise direct printing of cellular materials are known and desired, at least in part, because they may allow cells to be deposited within a 3D scaffold. For example, ink jet printing technology has been used to print biological materials. However, the shear force involved with propelling droplets of fluid onto a substrate can damage cells dispersed in the fluid. Further, ink jet printing is a slow process, which makes it challenging to adapt to biological materials, which require specific environmental conditions for survival.

Other systems for directly printing cells within a 3D structure include U.S. Pat. No. 8,639,484, which relates to use of a CAD model and a 3D positioning unit to deposit cellular materials through a multitude of nozzles, layer by layer, to create a 3D object. Multiple nozzles allow for multiple different materials to be included in the 3D object. US Patent Application Publication No: 2012/0089238 discloses a multi cartridge print system for producing composite organic 3D structures, whereby the structure is built using at least two syringes, one comprising a structural support polymer and another comprising a living cell composition, that iteratively deposit the structural support polymer and living cell composition on a surface. US Patent Application Publication No: 2014/0012407 discloses a device comprising one or more print heads, each configured to receive and hold one or more cartridges. Each cartridge comprises a fluid, such as a bio-ink comprising cells or support material, and an orifice wherefrom the fluid can be dispensed from the cartridge.

The prior art methods generally require multiple nozzles and/or cartridge orifices in order to facilitate printing of multiple different materials (i.e., one material is dispensed by one nozzle or cartridge orifice). Use of multiple nozzles for dispensing different materials requires a corresponding increase in movement of the printing system in order to position the appropriate nozzle or cartridge orifice in a controlled sequence to dispense a sequence of different materials. Such increased movement decreases speed and efficiency of printing.

It is desirable to obviate or mitigate one or more of the above deficiencies.

SUMMARY OF THE INVENTION

In a first aspect, a system for additive manufacturing of three-dimensional structures is provided. The system comprises at least one a print head for receiving and dispensing materials, the materials comprising a sheath fluid and a hydrogel. In one embodiment, the print head comprises an orifice for dispensing the materials; microfluidic channels comprising one or more first channels for receiving and directing the sheath fluid and one or more respective second channels for receiving and directing the hydrogel, the second channels intersecting at a first intersection point with the first channels, the second and first channels joining together at the first intersection point to form a dispensing channel which extends to the orifice; and fluidic switches, each fluidic switch corresponding to one of the microfluidic channels in the print head and configured to allow or disallow fluid flow in the microfluidic channels of the print head when actuated. In one embodiment, the system further comprises a receiving surface for receiving a first layer of the materials dispensed from the orifice; a positioning unit for positioning the orifice of the print head in three dimensional space, the positioning unit operably coupled to the print head; and a dispensing means for dispensing the materials from the orifice of the print head.

In one embodiment of the first aspect, the system comprises a programmable control processor for controlling the positioning unit and for controlling dispensing of the materials from the print head onto the receiving surface.

In one embodiment of the first aspect, the one or more first channels comprise at least two channels, the one or more first channels being configured to flank respective second channels at the first intersection point.

In one embodiment of the first aspect, the sheath fluid comprises a cross-linking agent for solidifying the hydrogel upon contact therewith at the intersection point and/or in the dispensing channel.

In one embodiment of the first aspect, each second channel has a diameter less than that of the first channels and the dispensing channel, whereby flow from the first channels forms a coaxial sheath around the hydrogel in the dispensing channel.

In one embodiment of the first aspect, the hydrogel comprises living cells.

In one embodiment of the first aspect, the system further comprises a fluid removal feature for removing excess sheath fluid from dispensed from the print head.

In one embodiment of the first aspect, the receiving surface comprises a porous membrane comprising pores sized to permit passage of the excess sheath fluid there through.

In one embodiment of the first aspect, the fluid removal feature comprises absorbent material or a vacuum for drawing the excess sheath fluid away from the receiving surface.

In one embodiment of the first aspect, the absorbent material or vacuum is applied below a porous membrane. In one embodiment of the first aspect, the vacuum is applied above the receiving surface.

In one embodiment of the first aspect, the vacuum is applied through one or more vacuum channels provided on the print head, the one or more vacuum channels having an orifice situated near the orifice of the print head.

In one embodiment of the first aspect, the system further comprises reservoirs for containing the materials, the reservoirs being fluidly coupled respectively to the microfluidic channels in the print head.

In one embodiment of the first aspect, the print head further comprises at least two inlets for receiving the materials from the reservoirs, each of the inlets being in fluid communication with respective microfluidic channels and the respective reservoirs.

In one embodiment of the first aspect, the dispensing means comprises a pressure control unit.

In one embodiment of the first aspect, the fluidic switches comprise valves.

In one embodiment of the first aspect, the print head further comprises a hollow projection configured to extend from the orifice toward the receiving surface.

In one embodiment of the first aspect, the print head comprises two second channels, each of the second channels being adapted to convey respective hydrogels, the two second channels intersecting at a second intersection and joining together at the second intersection to form a third channel which extends to the first intersection point.

In a second aspect, a system for additive manufacturing of three-dimensional structures is provided, the system comprising at least one a print head for receiving and dispensing materials, the materials comprising a sheath fluid and a hydrogel. In one embodiment, the print head comprises an orifice for dispensing the materials; microfluidic channels for receiving and directing the materials to the orifice; and fluidic switches, each fluidic switch corresponding to one of the microfluidic channels in the print head and configured to allow or disallow fluid flow in the microfluidic channels in the print head when actuated. In one embodiment, the system further comprises a receiving surface for receiving the materials dispensed from the orifice; a fluid removal feature for removing excess sheath fluid dispensed from the orifice; a positioning unit for positioning the orifice of the print head in three dimensional space, the positioning unit operably coupled to the print head; and a dispensing means for dispensing the materials from the orifice of the print head.

In one embodiment of the second aspect, the fluid removal feature comprises a vacuum for drawing the excess sheath fluid away from or through the receiving surface and/or from the hydrogel dispensed on the receiving surface.

In one embodiment of the second aspect, the receiving surface comprises a porous membrane comprising pores sized to permit passage of the excess sheath fluid there through.

In one embodiment of the second aspect, the vacuum is applied below the porous membrane. In one embodiment of the second aspect, the vacuum is applied above the receiving surface.

In one embodiment of the second aspect, the vacuum is applied through one or more vacuum channels provided on the print head, the one or more vacuum channels having an orifice situated near the orifice of the print head.

In one embodiment of the second aspect, the fluid removal feature comprises an absorbent material for drawing away from the receiving surface the excess sheath fluid.

In one embodiment of the second aspect, the system further comprises a programmable control processor for controlling the positioning unit and for controlling dispensing of the materials from the print head onto the receiving surface.

In one embodiment of the second aspect, the print head further comprises a hollow projection configured to extend from the orifice toward the receiving surface.

In one embodiment of the second aspect, the print head comprises one or more first channels for receiving and directing the sheath fluid and one or more respective second channels for receiving and directing the hydrogel, the second channels intersecting at a first intersection point with the first channels, the second and first channels joining together at the first intersection point to form a dispensing channel which extends to the orifice.

In one embodiment of the second aspect, the print head comprises two second channels, each of the second channels being adapted to convey respective hydrogels, the two second channels intersecting at a second intersection and joining together at the second intersection to form a third channel which extends to the first intersection point.

In a third aspect, a method of printing a three-dimensional (3D) structure is provided, the method comprising providing a 3D printer, the printer comprising: a print head comprising an orifice for dispensing materials; a receiving surface for receiving a first layer of the materials dispensed from the orifice of the print head; and a positioning unit operably coupled to the print head, the positioning unit for positioning the print head in three dimensional space. In one embodiment, the method comprises providing the materials to be dispensed, the materials to be dispensed comprising a sheath fluid and one or more hydrogels; encoding the printer with a 3D structure to be printed; dispensing from the print head orifice the materials to be dispensed; depositing a first layer of the dispensed materials on the receiving surface; repeating the depositing step by depositing subsequent dispensed material on the first and any subsequent layers of deposited material, thereby depositing layer upon layer of dispensed materials in a geometric arrangement according to the 3D structure; and removing excess sheath fluid dispensed by the print head orifice at one or more time point during or between depositing steps.

In one embodiment of the third aspect, the sheath fluid comprises a cross-linking agent suitable for cross-linking and solidifying the hydrogel upon contact therewith, the contact creating a hydrogel fiber.

In one embodiment of the third aspect, the sheath fluid and the hydrogel are dispensed in a coaxial arrangement, wherein the sheath fluid envelops the hydrogel.

In one embodiment of the third aspect, the depositing step and the removing step are carried out continuously, thereby continuously removing the excess sheath fluid as the layers of dispensed materials are deposited.

In one embodiment of the third aspect, the removing step is carried out intermittently between and/or at the same time as the depositing step, thereby intermittently removing the excess sheath fluid as the layers of dispensed materials are deposited.

In one embodiment of the third aspect, the one or more hydrogels are adapted for supporting growth and/or proliferation of living cells dispersed therein.

BRIEF DESCRIPTION OF THE DRAWINGS

The features of the invention will become more apparent in the following detailed description in which reference is made to the appended drawings wherein.

DETAILED DESCRIPTION OF THE INVENTION

Figure 1:
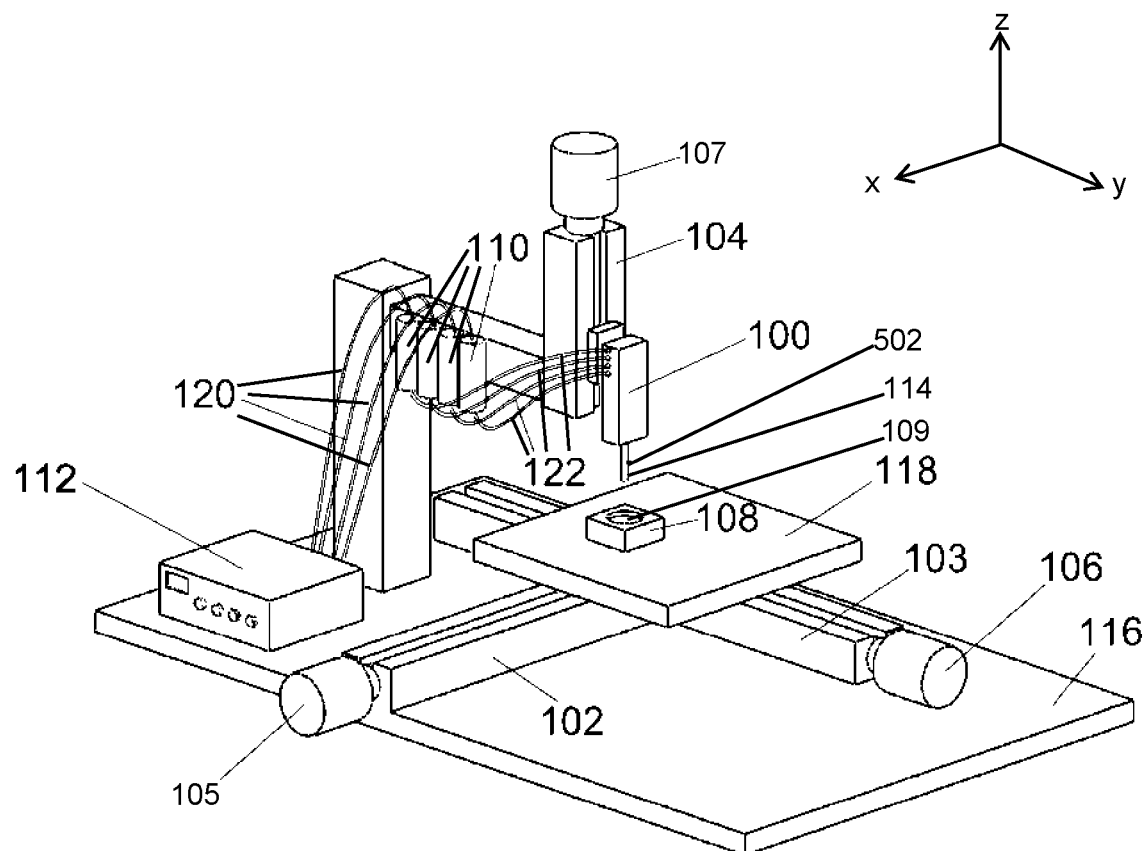
FIG. 1 is a perspective view of one embodiment of the printing system of the present invention.

The definitions of certain terms as used in this specification are provided below. Unless defined otherwise, all technical and scientific terms used herein generally have the same meaning as commonly understood by one of ordinary skill in the art to which this invention belongs.

As used herein, the term "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

As used herein, the term "hydrogel" refers to a composition comprising water and a network or lattice of polymer chains that are hydrophilic. Examples of natural hydrogels include, for example, alginate, agarose, collagen, fibrinogen, gelatin, chitosan, hyaluronic acid based gels or any combination thereof. A variety of synthetic hydrogels are known and could be used in embodiments of the systems and methods provided herein. For example, in embodiments of the systems and method provided herein, one or more hydrogels form the structural basis for three dimensional structures printed. In some embodiments, the hydrogel has the capacity to support growth and/or proliferation of one or more cell types, which may be dispersed within the hydrogel or added to the hydrogel after it has been printed in a three dimensional configuration. In some embodiments, the hydrogel is cross-linkable by a chemical cross-linking agent. For example, a hydrogel comprising alginate may be cross-linkable in the presence of a divalent cation, a hydrogel comprising fibrinogen may be cross-linkable in the presence of thrombin, and a hydrogel comprising collagen or chitosan may be cross-linkable in the presence of heat or a basic solution. Cross-linking of the hydrogel will increase the hardness of the hydrogel, in some embodiments allowing formation of a hydrogel that behaves like a solid.

As used herein, the term "sheath fluid" refers to a liquid that is used, at least in part, to envelope or "sheath" a material to be dispensed, such as, for example, a hydrogel. In some embodiments, the sheath fluid comprises one or more of an aqueous solvent, for example water or glycerol, and a chemical cross-linking agent, for example materials comprising divalent cations (e.g. $Ca^{2+}$, $Ba^{2+}$, $Sr^{2+}$, etc.), thrombin, or pH modifying chemicals such as sodium bicarbonate.

As used herein, the term "excess sheath fluid" refers to a portion of the sheath fluid that is dispensed from the print head orifice and does not form part of a three dimensional structure printed using one or more embodiments of the systems or methods provided herein. For example, the excess sheath fluid may be useful in lubricating passage of the hydrogel through a dispensing channel in the print head and through the print head orifice. Once dispensed from the print head orifice the excess sheath fluid may run off of the surface of a layer of dispensed hydrogel and onto a receiving surface, where it may collect or pool.

As used herein, the term "receiving surface" refers to the surface upon which a first layer of material dispensed from a print head orifice is deposited. The receiving surface also receives excess sheath fluid that is dispensed from the print head orifice and that runs off of one or more layers of material dispensed from the print head orifice. In some embodiments, the receiving surface is made of a solid material. In some embodiments, the receiving surface is made of a porous material. For example, in some embodiments, the porosity of the porous material is sufficient to allow passage of the sheath fluid there through. In some embodiments, the receiving surface is substantially planar, thereby providing a flat surface upon which a first layer of dispensed material can be deposited. In some embodiments, the receiving surface has a topography that corresponds to the three dimensional structure to be printed, thereby facilitating printing of a three dimensional structure having a non-flat first layer.

In one aspect, the present invention generally relates to an apparatus, system and method for additive manufacturing of three-dimensional (3D) biological structures.

General Description of the Printing System

In an aspect, the invention provides a system for additive manufacturing of three-dimensional structures (also referred to herein as a "printer", a "3D printer" or a "printing system" or "the system"). The system comprises a microfluidic print head, which is a microfluidic liquid handling device comprising one or more microfluidic channels for receiving and directing materials to be dispensed, fluidic switches corresponding to the microfluidic channels for regulating flow of the materials to be printed, and a single orifice for dispensing the materials to be dispensed.

The materials to be dispensed comprise a sheath fluid and at least one hydrogel. In a preferred embodiment, the sheath fluid comprises a chemical cross-linking agent suitable for solidifying the hydrogel upon contact therewith. In a preferred embodiment, the sheath fluid also serves as a lubricant for the solidified hydrogel.

The microfluidic channels serve as conduits for directing and combining the materials to be dispensed in a controlled manner. The microfluidic channels are arranged within the print head such that one or more first channels for receiving and directing the sheath fluid and a second channel for receiving and directing the hydrogel intersect at a first intersection point and join together to form a dispensing channel which extends to the orifice of the print head. In one preferred embodiment, the first channels are configured to flank the second channel at the first intersection point. In this way, the sheath fluid is directed to flow along either side of the hydrogel in the dispensing channel.

In a preferred embodiment, materials in the dispensing channel are directed coaxially, the hydrogel being focussed to the center of the dispensing channel and the sheath fluid surrounding the hydrogel fluid, thereby forming a sheath around the hydrogel. In preferred embodiments where the sheath fluid also comprises a chemical cross-linking agent suitable for cross-linking the hydrogel, a solidified hydrogel fiber is formed in the dispensing channel and dispensed from the orifice of the print head.

In one aspect, the system further comprises a receiving surface for receiving a first layer of the materials dispensed from the orifice and a positioning unit for positioning the orifice of the print head in three dimensional space, the positioning unit operably coupled to the print head. For example, the print head can be coupled to a commercially available motorized positioning system with three degrees of motion so that the print head can be positioned above the receiving surface and oriented to direct dispensed material downward towards the receiving surface.

In one aspect, the system comprises a means for dispensing the materials from the print head orifice and may further comprise and/or be in data communication with a programmable control processor for regulating positioning of the print head orifice. The programmable control processor may also be used for regulating dispensing of the materials to be dispensed from the print head orifice.

FIG. 1 shows a schematic perspective view of one embodiment of the 3D printing system provided herein.

Referring to FIG. 1, the system comprises a microfluidic print head [100], which comprises a print head orifice [114] and at least one inlet for receiving material to be dispensed from the print head [100]. The material to be dispensed is stored in printed material reservoirs [110] and delivered to the print head through respective first connecting tubes [122], which provide fluid communication between the print head and the printed material reservoirs. In the illustrated embodiment, the means for dispensing the material to be dispensed from the print head orifice is a pressure control unit [112], which is fluidly coupled to the printed material reservoirs [110] by respective second connecting tubes [120]. The pressure control unit is a means for providing a force to dispense the materials to be dispensed. The pressure control unit supplies pneumatic pressure to the printed material reservoirs [110] via respective second connecting tubes [120]. The pressure applied to the printed material reservoirs forces fluid out of the reservoirs and into the print head via respective first connecting tubes [122]. Alternative means for dispensing the material to be dispensed could be used in the illustrated embodiment. For example, a series of electronically controlled syringe pumps could be used to provide force for dispensing the material to be dispensed from the print head orifice.

Referring to FIG. 1, the microfluidic print head [100] is coupled to a 3D motorized stage comprising three arms [102, 103 and 104] for positioning the print head and the print head orifice [114] in three dimensional space above a print bed [108], which comprises a surface [109] for receiving printed material. In one embodiment, the 3D motorized stage (i.e., the positioning unit) can be controlled to position a vertical arm [104], which extends along the z-axis of the 3D motorized stage such that the print head orifice is directed downward. A first horizontal arm [102], which extends along the x-axis of the motorized stage is secured to an immobile base platform [116]. A second horizontal arm [103], which extends along the y-axis of the motorized stage is moveably coupled to an upper surface of the first horizontal arm [102] such that the longitudinal directions of the first and second horizontal arms [102 and 103] are perpendicular to one another. It will be understood that the terms "vertical" and "horizontal" as used above with respect to the arms are meant to describe the manner in which the print head is moved and do not necessarily limit the physical orientation of the arms themselves.

In the embodiment illustrated in FIG. 1, the print-bed [108] is positioned on top of a platform [118], the platform being coupled to an upper surface of the second horizontal arm [103]. In the embodiment, the 3D motorized stage arms [102, 103 and 104] are driven by three corresponding motors [105, 106 and 107], respectively, and controlled by a programmable control processor, such as a computer (not shown). In a preferred embodiment, the print head [100] and print-bed [108] are collectively moveable along all three primary axes of a Cartesian coordinate system by the 3D motorized stage and movement of the stage is defined using computer software.

It will be understood that the invention is not limited to only the described positioning system and that other positioning systems are known in the art.

Figure 2:
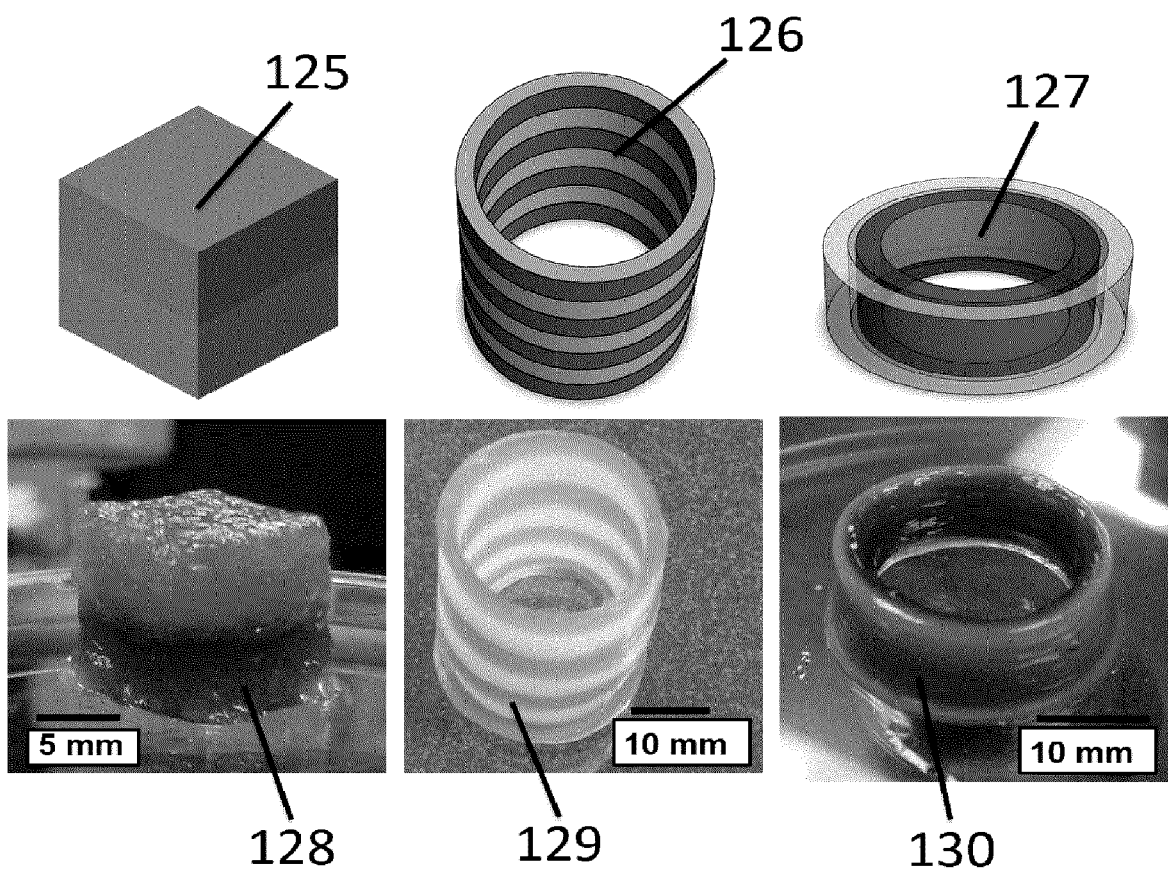
FIG. 2 is a perspective view of software-designed objects and corresponding objects printed using one embodiment of the printing system of the present invention.

In the embodiment illustrated in FIG. 1, as material is dispensed from the print head orifice [114], the positioning unit is moved in a pattern controlled by software, thereby creating a first layer of the dispensed material on the receiving surface [109]. Additional layers of dispensed material are stacked on top of one another such that the final 3D geometry of the dispensed layers of material is generally a replica of the 3D geometry design provided by the software. The 3D design may be created using typical 3D CAD (computer aided design) software or generated from digital images, as known in the art. Further, if the software generated geometry contains information on specific materials to be used, it is possible, according to one embodiment of the invention, to assign a specific material type to different geometrical locations. For example, FIG. 2 shows three 3D structures printed using one embodiment of the system provided herein: a cube [128], a hollow cylinder [129] and a hollow coaxial cylinder [130]. Software was used to generate cube, hollow cylinder and hollow coaxial cylinder designs ([125], [126] and [127], respectively), each design comprising two different types of materials (dyed alginate), which were dyed different colors to provide visual clarity of the materials used to generate the printed cube and hollow cylinder.

Any software, application or module referred to herein may be implemented using computer readable/executable instructions that may be stored or otherwise held by such computer readable media.

Print Head

Figure 3:
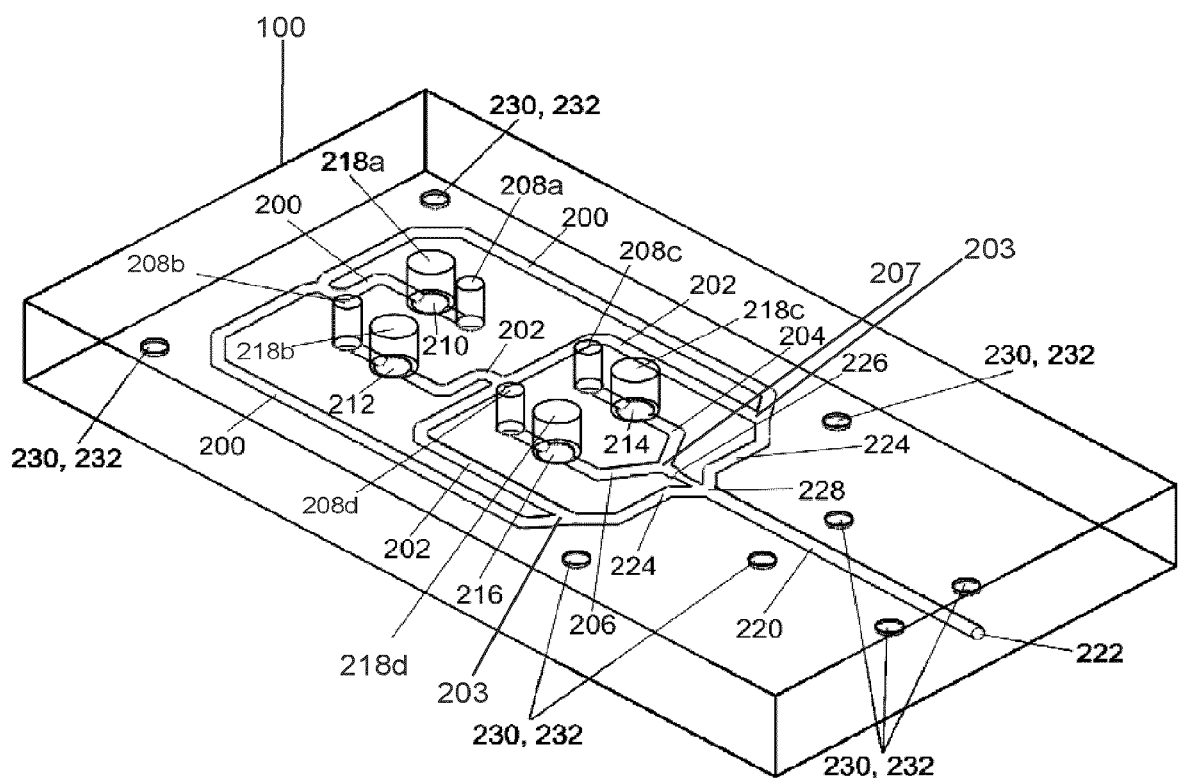
FIG. 3 is a perspective view of one embodiment of the print head of the present invention.

FIG. 3 shows a schematic perspective view of one embodiment of a microfluidic print head [100] for use in the system provided.

Referring to FIG. 3, the illustrated embodiment depicts a microfluidic print head [100] comprising microfluidic channels for carrying various fluids. In the illustrated embodiment, the microfluidic channels have a cylindrical shape. However, channel shapes other than cylindrical could also be used in the print head provided herein. Channel [200] is a conduit for a cross-linking agent, channel [202] is a conduit for water. In the illustrated embodiment, the cross-linking agent and water, separately or together serve as the "sheath fluid". Channel [204] is a conduit for a first hydrogel composition (referred to as "hydrogel A"), and channel [206] is a conduit for a second hydrogel composition (referred to as "hydrogel B"). In a preferred embodiment, one or more living cell types are compatible with and optionally dispersed within hydrogels A and/or B. In the illustrated embodiment, each microfluidic channel comprises a fluid inlet [208a, 208b, 208c, 208d], which allows fluid contained in the connecting tubes [122] to pass into the respective channels of the print head [100]. Downstream of the fluid inlets [208a, 208b, 208c, 208d] are valves [210, 212, 214, 216] corresponding to each channel. In the illustrated embodiment, the valves serve as "fluidic switches", which can be actuated to allow and disallow flow of fluid through a channel, each valve having a corresponding inlet [218, 218a, 218b, 218c, 218d], which facilitates actuation and de-actuation of the valve. In one embodiment, the valves [210, 212, 214, 216] can be electronically actuated. In another embodiment, the valves [210, 212, 214, 216] can be actuated by a change in applied pressure, for example, by way of solenoid pistons. Electronic or pressure actuation of different valves facilitates rapid change of the material dispensed, thereby allowing the materials dispensed to be composed of a controlled sequence of different materials.

Referring further to FIG. 3, in the illustrated embodiment, the crosslinking agent channels [200] and water channels [202] intersect at intersection points [203], such as in a "y-shaped" configuration, joining together to form channels referred to herein as "sheath flow channels" [224] immediately downstream of the crosslinking agent and water channels [200, 202]. The hydrogel A and hydrogel B channels [204, 206] intersect at an intersection point [207], such as in a "y-shaped" configuration, joining together to form a channel referred to herein as a "focussing channel" [226] immediately downstream of the two hydrogel channels. The sheath flow channels [224] and the focussing channel [226] intersect at an intersection point [228] in a three-pronged configuration, for the described embodiment, wherein the focussing channel [226] is flanked by the sheath flow channels [224], joining together to form a channel referred to herein as a dispensing channel [220]. The dispensing channel [220] terminates in the dispensing orifice [222]. In a preferred embodiment illustrated in FIG. 1, the dispensing channel projects from the print head [100] terminating in the dispensing orifice [114].

Referring further to FIG. 3, in the illustrated embodiment, the sheath flow channels [224] and the dispensing channel [220] have larger diameters than the focussing channel [226]. When hydraulic pressure is applied to the sheath flow [224] and focussing channels [226], liquid in the focussing channel [226] is compressed laterally and "focussed" into a narrow stream along the central axis of the focussing channel [226]. Upon intersection with the focussing channel [226] at the intersection point [228], fluid from the larger diameter sheath flow channels [224] surrounds and envelopes the narrower focussed stream of hydrogel dispensed from the focussing channel [226].

In a preferred embodiment, liquid in the sheath flow channels [224] comprises a chemical cross-linking agent and liquid in the focussing channel [226] comprises one or more chemically cross-linkable hydrogels comprising one or more living cell types. When the one or more chemically cross-linkable hydrogels are focussed into a narrow stream in the focussing channel [226] and then enveloped by the cross-linking agent in the dispensing channel [220], at least the exterior surface of the one or more chemically cross-linkable hydrogels is solidified in the dispensing channel [220], thereby creating a cross-linked or "solid" hydrogel fiber. The hydrogel fiber is then dispensed from the dispensing orifice [222] onto the receiving surface in a controlled manner, building a 3D structure, layer by layer.

In a particularly preferred embodiment, the sheath fluid surrounding the hydrogel fiber may also act to lubricate passage of the hydrogel fiber through the dispensing channel [220] until it is dispensed from the print head orifice [222].

In an embodiment, the sheath fluid comprises a chemical cross-linking agent, water or a combination thereof. In embodiments where the sheath fluid lacks a chemical cross-linking agent the hydrogel will not be solidified and would be dispensed as a liquid. In order to adjust the composition of the sheath fluid and start and/or stop solidification of the hydrogel, a crosslinking agent channel valve [210] and water channel valve [212] may be actuated. It is contemplated that dispensing a liquid rather than a solid hydrogel, or dispensing sheath fluid alone, may be desirable in order to construct some aspects of various three dimensional objects.

In an embodiment, the print head [100] may be configured to receive and dispense only one hydrogel material. In one embodiment, the print head may be configured to receive and dispense two or more hydrogel materials. For example, in an embodiment where the print head [100] is configured to receive two hydrogel materials, each, for example, comprising a different cell type, the system provided herein can be programed to dispense a heterogeneous cellular structure, wherein first and second cell types can be laid down in controlled patterns within and among layers, alone and/or in combination with one another. Boundaries between the two materials are controlled, e.g., by software, and the programmable control processor is used to instruct fluidic switched (e.g., one or more of valves [210], [212], [214], [216]) to change the flow of material within one or more microfluidic channels, thereby changing the content of the material being dispensed from the print head orifice. The number of hydrogel materials that can be received by and dispensed from the print head provided herein is limited only by the size of the print head that the user deems practical.

Figure 4:
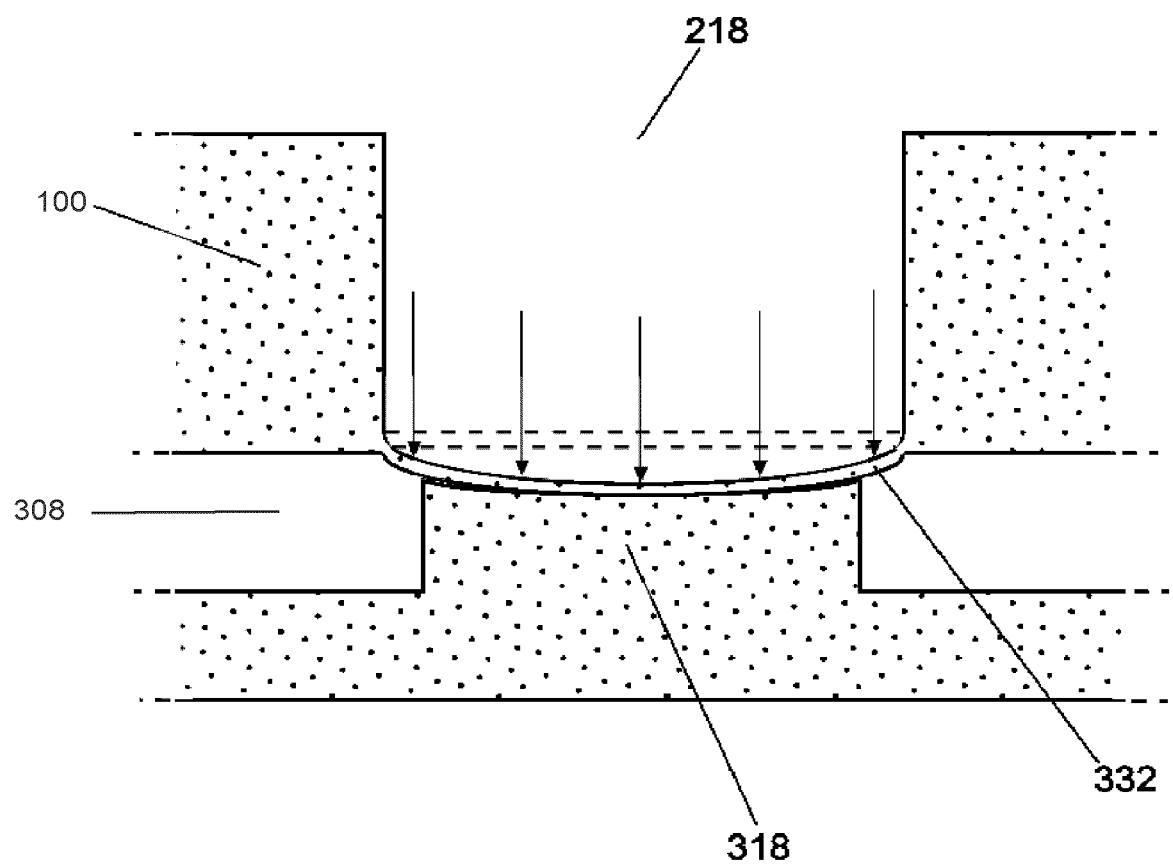
FIG. 4 is a cross-section of a valve in the print head of FIG. 3, including deflection of a valve membrane when the valve is actuated.

Referring to FIG. 4, in one embodiment, the fluidic switch is a valve comprising a membrane [332] disposed over a bowl-shaped feature [318] formed in a microfluidic channel [308]. Upon application of pneumatic pressure (represented by arrows in FIG. 4) to the exposed surface of the valve membrane [332], the valve membrane [332] will be deflected into the bowl shaped feature [318], thereby blocking passage of fluid through microfluidic channel [308]. In one preferred embodiment, the thickness of the valve membrane [332] is about 150 μm. In embodiments where the valve membrane thickness is increased, a skilled person would understand that the applied pneumatic valve actuation pressure must be increased accordingly. Similarly, a valve membrane formed of less resilient material will require a higher actuation pressure. A skilled person would understand how to adjust the actuation pressure to suit the specific material of the valve membrane.

In one embodiment, the print head comprises alternative fluidic switches for regulating materials to be dispensed from the print head orifice. For example, rather than using valves, a mechanism for engaging or disengaging the pressure applied to each channel could be used to regulate material flow in the microfluidic channels.

Figure 5:
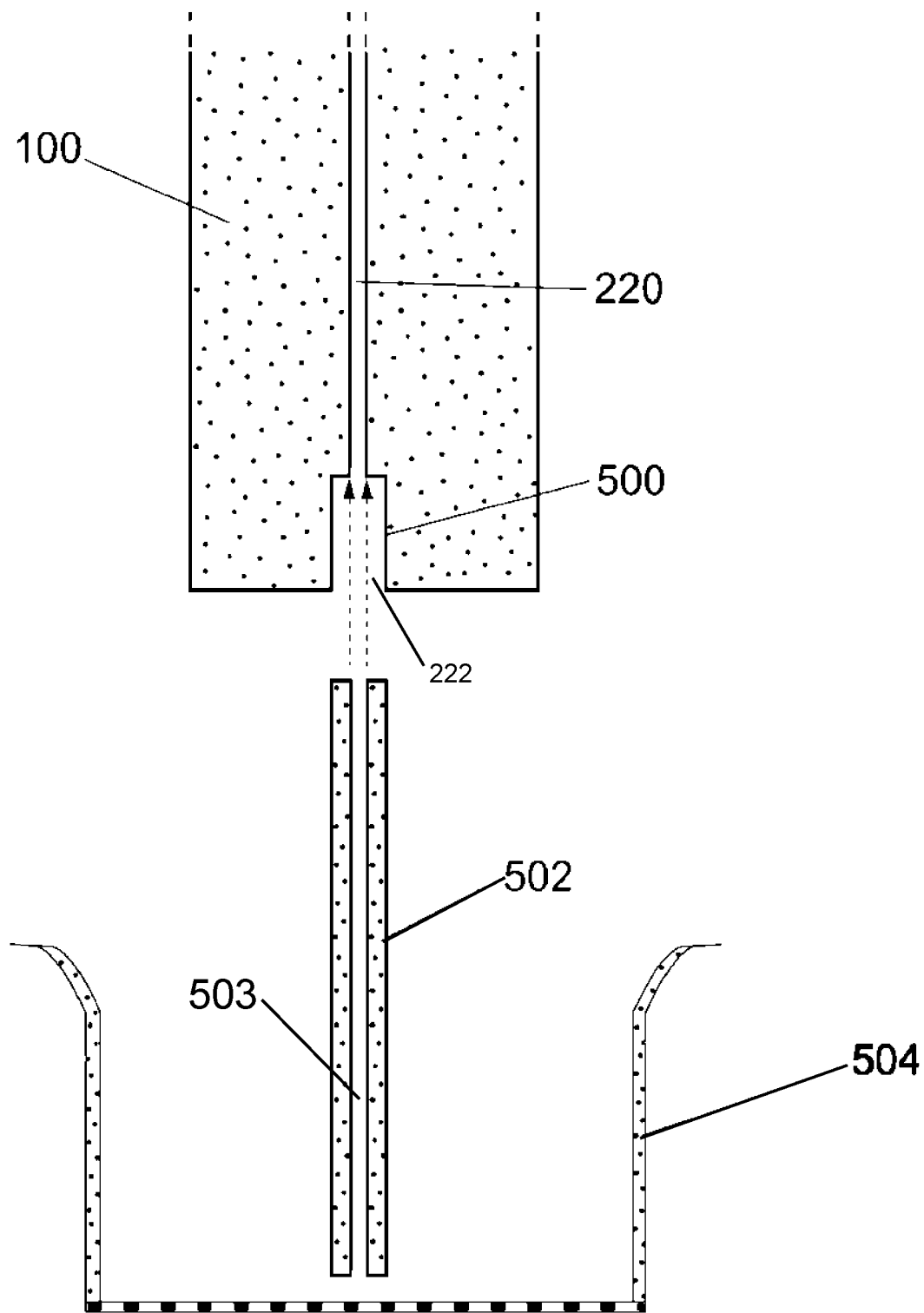
FIG. 5 is a cross-section of an alternate embodiment of the print head of FIG. 3.

In one embodiment, the print head further comprises an extension tip comprising an orifice for dispensing materials from the print head. Such an extension tip facilitates precision dispensing of materials and deposition thereof in confined areas such as, for example, a well in a multi-well plate (e.g., a standard microtitre plate, microwell plate or microplate having 6, 24, 96 etc. wells) or a petri dish. Referring to the embodiment illustrated in FIG. 5, a portion [500] of the dispensing channel [220] nearest to the dispensing orifice [222] has a larger diameter than the upstream portion of the dispensing channel [220]. The extension tip [502] comprises a tube (e.g., made of plastic, glass or metal) having an exterior configured to fit into the large-diameter portion [500] of the dispensing channel and an inner surface (defining a hollow space in the tube) configured to align with the dispensing channel [220]. The extension tip [502] can be inserted into the large-diameter portion [500] of the dispensing channel, thereby, extending the length of the dispensing channel [220], which facilitates deposition of material dispensed from an orifice [503] in the extension tip [502] into confined spaces, such as a well plate insert [504] or petri dish (not shown).

Referring to the embodiment illustrated in FIG. 1, the extension tip [502] is a projection extending from the print head [100], the extension tip [502] terminating in the print head orifice [114]. In this embodiment, the extension tip [502] is integral with the print head.

Figure 6:
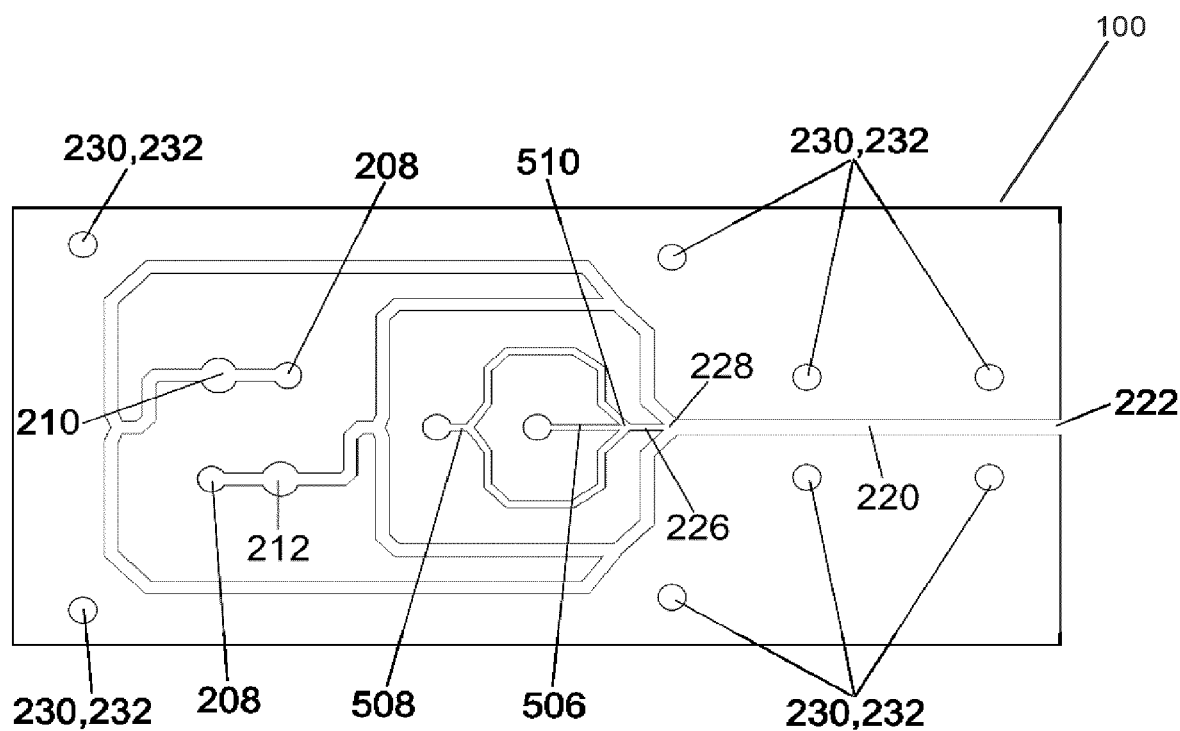
FIG. 6 is a top view of an alternate embodiment of the print head of FIG. 3.

In one embodiment, two or more hydrogel materials can be arranged coaxially in a hydrogel fiber dispensed from the system provided herein. Referring to FIG. 6, in the illustrated embodiment, the print head [100] comprises microfluidic channels arranged to produce a coaxial hydrogel fiber comprising a hydrogel core material and hydrogel shell material. In the illustrated embodiment, the shell material, carried in channels [508], is a rapidly gelling hydrogel, such as alginate, and the core material, carried in channel [506], is a different hydrogel chosen by the user (e.g. collagen or fibrinogen). Channels [508] and channel [506] intersect at a hydrogel focussing intersection point [510], for example in a "y-shaped" configuration (similar to intersection [228] shown in FIG. 3) joining together to form a focussing channel [226] downstream of channels [506] and [508]. At the hydrogel focussing intersection [510], the shell material focusses the core material coaxially such that the shell material forms a sheath around the core material. In preferred embodiments, channels [508] and [226] have a larger diameter than channel [506] to facilitate coaxial focussing of the core and shell materials. In a preferred embodiment, the purpose of the shell material is to provide the core material with physical structural support so that it may be formed into a 3D geometry. The core may be solidified after the material is deposited, the precise method of solidification being specific to different core materials. For example, the core may comprise a material that solidifies very slowly. In another embodiment, the core and shell materials comprise the same materials. In yet another embodiment, the shell material comprises a hydrogel that rapidly solidifies and the core material comprises a material that will not gel, thereby facilitating generation of a hollow fiber.

In one embodiment, the print head [100] depicted in FIG. 6 could further comprise additional core material channels, each with a corresponding fluidic switch, for example a valve, for regulating flow of the material therein. The fluidic switch facilitates rapid and frequent adjustments to the composition of the core material in the fiber being dispensed, for example, by commands provided by the programmable control processor.

In one embodiment, several print heads could be arranged, for example in parallel, to allow simultaneous printing of multiple structures. This would increase throughput production.

In some embodiments the print head is disposable. Use of disposable print heads can reduce the likelihood of contamination of materials used in different print jobs.

The print head can be fabricated for example, using known microfluidics molding techniques (e.g., casting, imprinting or injection molding) and one or more moldable polymers, for example, polydimethylsiloxane (PDMS). Alternatively, commercially available 3D printing technology could be used to fabricate the print head. As depicted in FIG. 3 and FIG. 6, [230] and [232] represent alignment holes between layers of the print head.

Fluidic Removal Feature

In an aspect, the invention provides a system for additive manufacturing of three-dimensional structures that comprises a feature for removing excess sheath fluid from the receiving surface where a first layer of material dispensed from the orifice of the print head is deposited and optionally from a surface of dispensed hydrogel. During printing, it is possible that excess sheath fluid will collect or "pool" on the receiving surface or on a surface of dispensed hydrogel. Such pooling can interfere with deposition of hydrogel dispensed from the print head orifice onto the receiving surface and/or onto one or more layers of dispensed hydrogel. For example, pooled sheath fluid may cause a dispensed hydrogel fiber to slip from its intended position in the 3D structure being printed. Therefore, in embodiments of the system, removal of excess sheath fluid from the receiving surface and optionally from a surface of the dispensed hydrogel by way of a fluidic removal feature may improve additive manufacturing of three-dimensional structures.

Excess sheath fluid may be removed from the receiving surface or from a surface of one or more layers of dispensed hydrogel by drawing the fluid off of those surfaces, by allowing or facilitating evaporation of the sheath fluid from those surfaces or, in embodiments where the receiving surface is porous, excess sheath fluid may be removed by drawing it through the porous surface.

In a preferred embodiment, the receiving surface comprises a porous material, the pores being sized to facilitate passage of sheath fluid there through and sized to support one or more layers of hydrogel deposited thereon.

Figure 7:
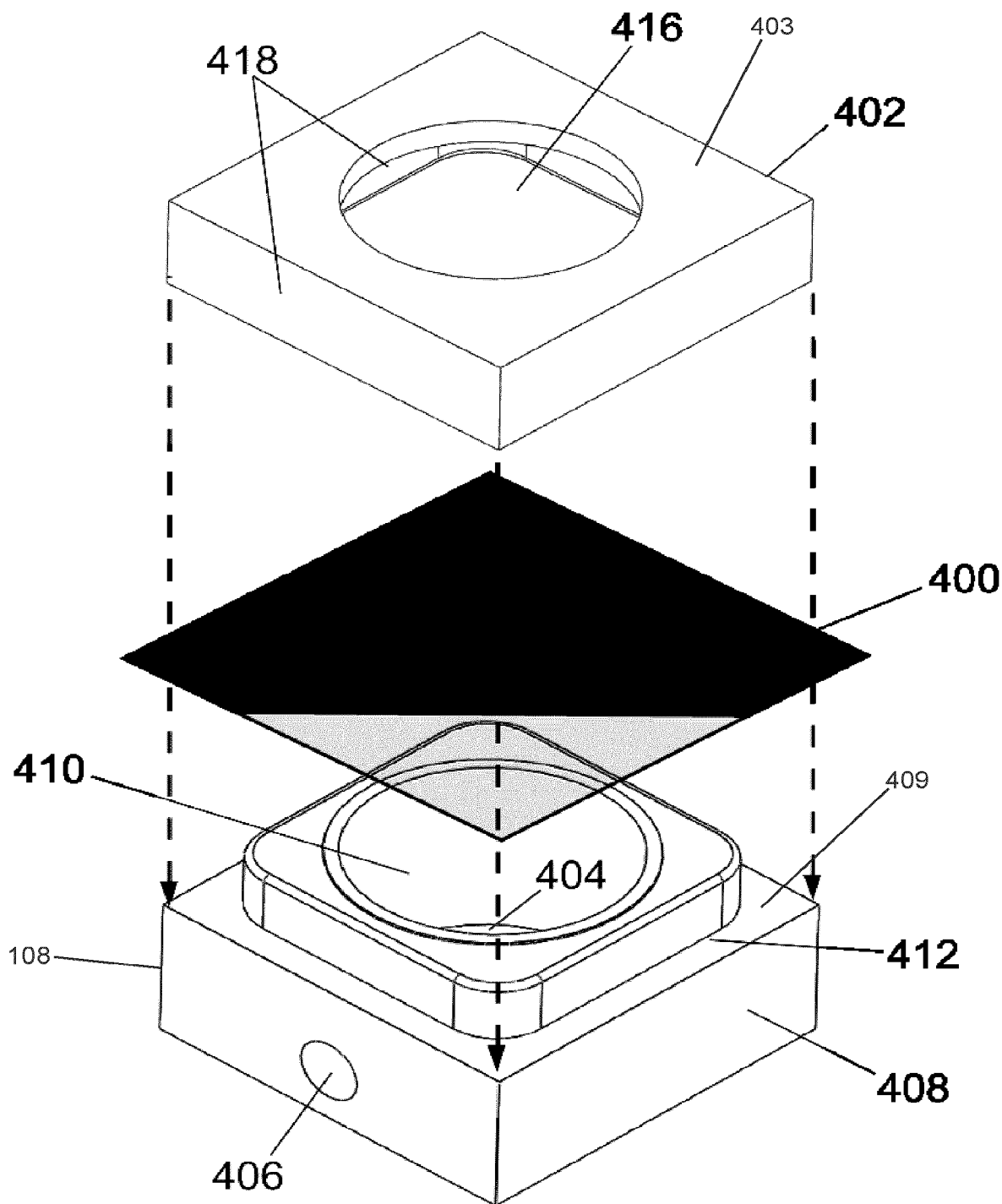
FIG. 7 is an exploded perspective view of one embodiment of the print-bed assembly of the present invention.
Figure 8:
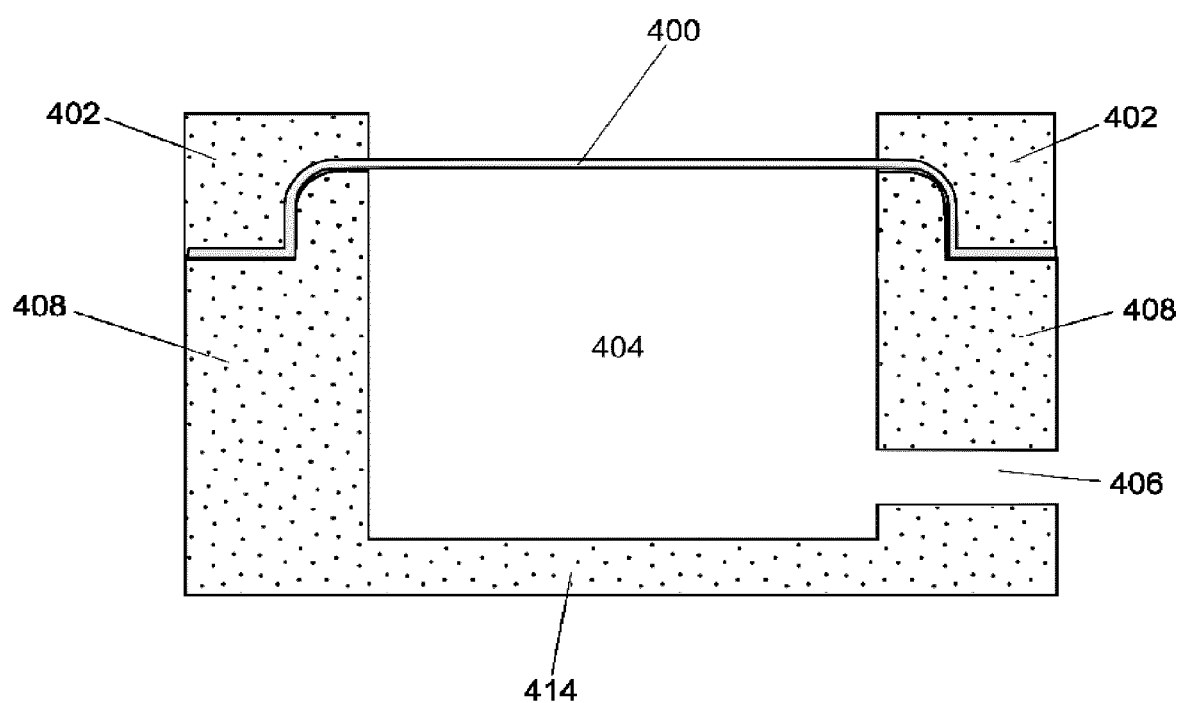
FIG. 8 is a cross-section of the assembled print-bed of FIG. 9.

Referring to FIGS. 7 and 8, in the illustrated embodiments, a print bed [108] comprises a porous membrane [400], which serves as the surface for receiving a first layer of dispensed material (i.e., the receiving surface). The porous membrane [400] is held in place in the print bed [108] between a box piece [408] and a lid piece [402]. The box piece [408] is a container, which can be any shape suitable for receiving and containing liquid (e.g., square, round). The space inside of the box piece [408] is referred to as a chamber [404]. The box piece [408] has an upper surface [409] comprising a recessed lip [412] extending the perimeter of the upper surface [409] of the box piece [408]. The upper surface [409] comprises an aperture defined by one or more walls [410], the aperture being surrounded by the recessed lip [412] and extending into the box piece [408].

Referring further to the embodiments illustrated in FIGS. 7 and 8, the lid piece [402] comprises an upper surface [403] having an aperture [416] that extends therethrough and sidewalls [418] configured to fit around the recessed lip [412] of the box piece [408], thereby facilitating placement of the lid piece [402] on the upper surface [409] of the box piece [408]. When the lid piece [402] is placed on the box piece [408] apertures in the box and the lid piece [416] align. In operation, the porous membrane [400] is placed on the upper surface [409] of the box piece [408] such that it extends over the aperture in the upper surface [409] of the box piece [408], the lid piece [402] is then placed on top of the box piece and pressed downward. The downward pressure of the lid piece [402] stretches the porous membrane [400] over the aperture in the upper surface [409] of the box piece [408], thereby retaining the porous membrane [400] between the box piece [408] and the lid piece [402]. In preferred embodiments, the lid piece [402] and box piece [408] fit together snuggly, thereby providing a connection that will remain secure during operation of the system provided herein.

Referring further to the embodiments illustrated in FIGS. 7 and 8, the box piece [408] comprises a solid base [414] and at least one outlet duct [406] for directing fluid away from the chamber [404], and a vacuum source (not shown) in fluid communication with the outlet duct [406] of the chamber [404]. The porous membrane [400] comprises pores sized to facilitate passage of sheath fluid. The vacuum source (not shown) coupled to the outlet duct [406] may be actuated to draw the excess sheath fluid collected on the porous membrane [400] through the porous membrane [400] into the chamber [404] and from the chamber [404] through the outlet [406], leaving the hydrogel fiber in its dispensed configuration on top of the porous membrane [400].

In a preferred embodiment, a feature for removing excess sheath fluid from the receiving surface and optionally from a surface of dispensed hydrogel can be included in a system configured to dispense materials into a multiwall plate or petri dish. For example, referring to FIG. 9, in the illustrated embodiment, a commercially available well-plate insert [504], is placed on top of the box piece [408]. Some well-plate inserts [504] have a basket shape with a base made out of a porous membrane material [512]. In the illustrated embodiment, a gasket [514] is placed between the well-plate insert [512] and the box piece [408] to improve sealing between the two pieces [504 and 408]. In such embodiments, the porous membrane [512] of the well-plate inset [504] would serve as the "receiving surface" and any excess sheath fluid could be removed therefrom using a vacuum coupled to the outlet duct [406], as described above, or using one of the other fluidic removal features described below.

Figure 9:
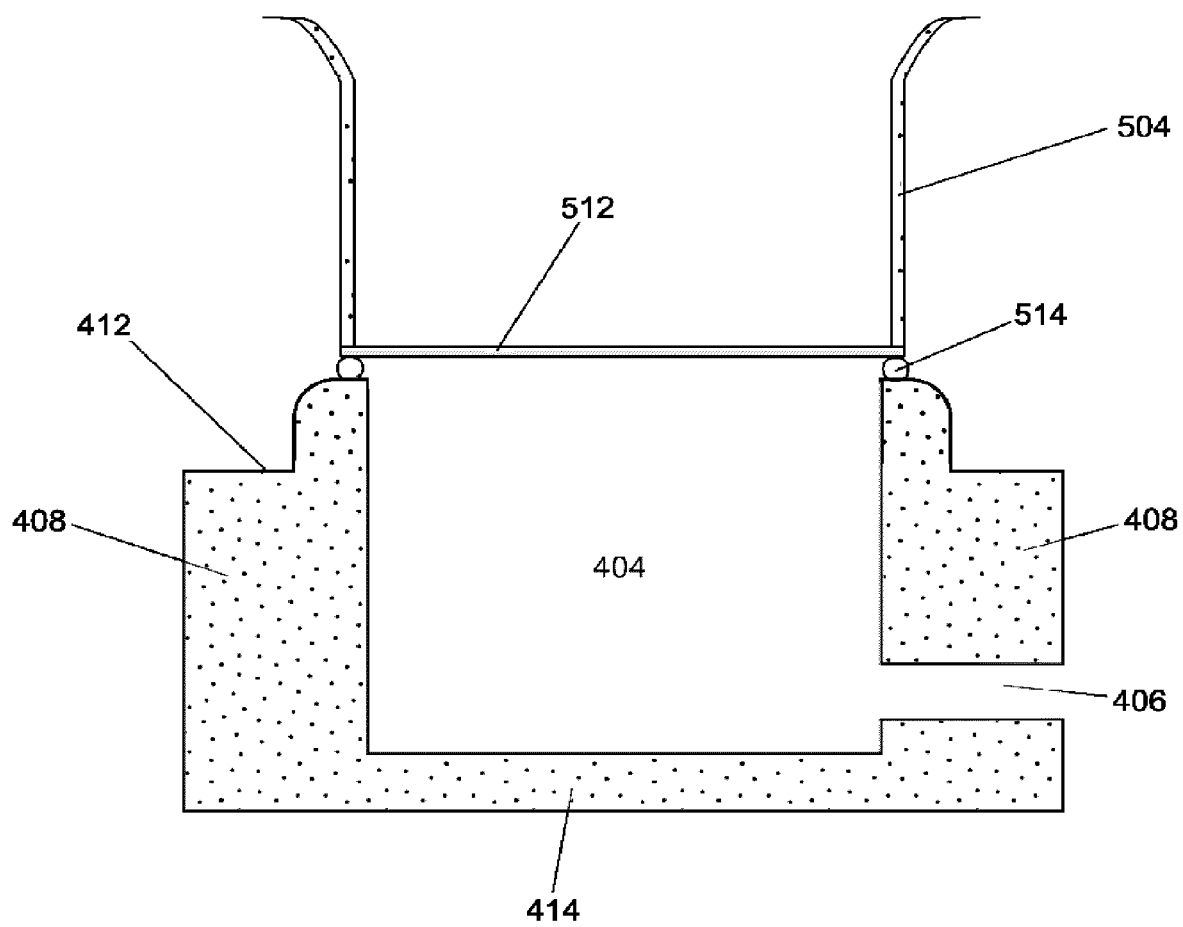
FIG. 9 is a cross-section of an alternate embodiment of the print-bed of FIG. 9.

In one embodiment (not shown), the receiving surface on the print bed comprises or is placed adjacent to an absorptive material, which facilitates absorption of excess sheath fluid from the receiving surface. For example, a well-plate insert having a base made out of a porous membrane material (for example, as shown in FIG. 9), or any other porous membrane substrate, could be placed on top of or adjacent to an absorptive material, such as, for example, a sponge. The absorptive material would act to draw away from the receiving surface excess sheath fluid. In embodiments where the absorbent material is disposed below a porous receiving surface, excess sheath fluid on the receiving surface would be drawn through the porous receiving surface and into the absorptive material, thereby preventing pooling of excess sheath fluid on the receiving surface. In embodiments where the absorbent material is disposed immediately beside or on top of a portion of the receiving surface (e.g., on the periphery of the receiving surface so as not to interfere with deposition of dispensed material) excess sheath fluid would be drawn off of the receiving surface and into the absorbent material.

In one embodiment (not shown), rather than using one of the print beds described above, one or more tubes may be provided in an area near the receiving surface and near the print head orifice. The one or more tubes may be fluidly coupled to a vacuum source (not shown), which can provide suction for removing excess sheath fluid from the receiving surface and optionally from a surface of dispensed hydrogel. In such embodiments, a solid or porous receiving surface may also be used.

Figure 10:
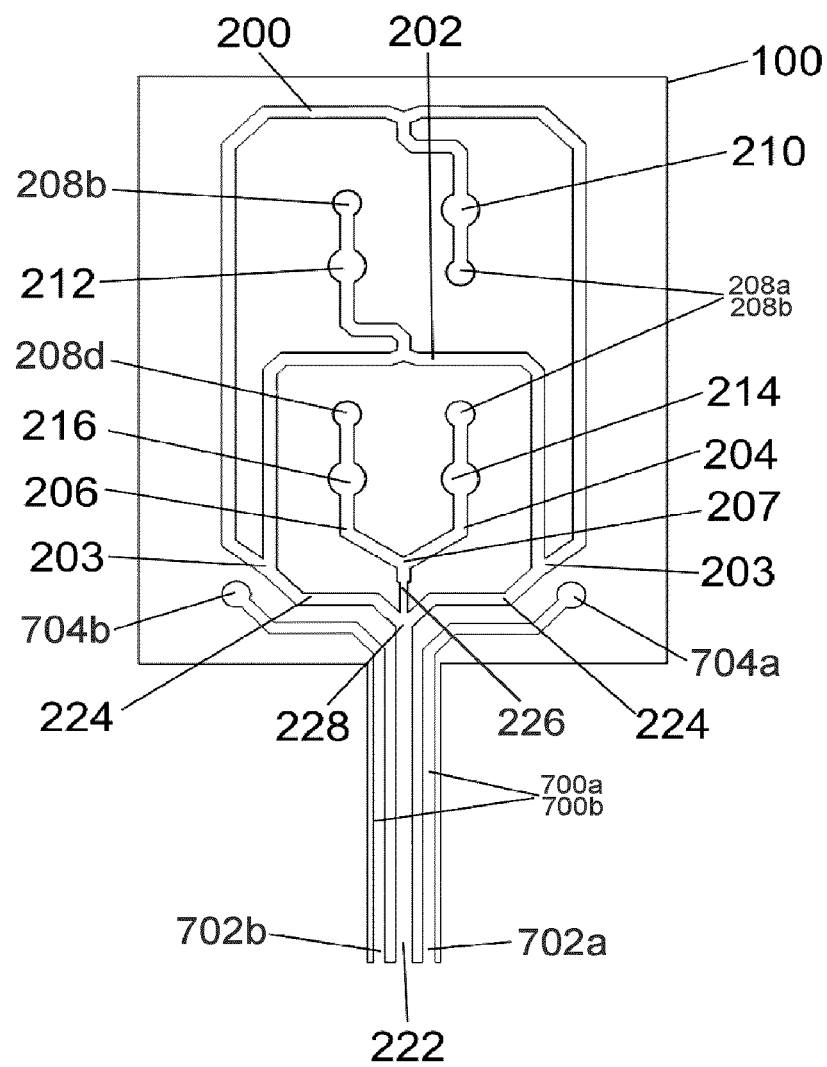
FIG. 10 is a perspective view of one embodiment of the print head of the present invention.

In one embodiment, illustrated in FIG. 10, the print head is configured to further comprise one or more vacuum channels [700a, 700b], the one or more vacuum channels each having an orifice [702a, 702b] situated near the print head orifice [222]. The one or more vacuum channels [700a, 700b] each have an inlet [704a, 704b] configured to facilitate fluid communication with one or more vacuums (not shown). When the print head [100] is in fluid communication with a vacuum, the one or more vacuum channels [702a, 702b] direct negative pressure to an area of the receiving surface where materials are being dispensed or have been dispensed from the print head orifice [222] and/or to a portion of the surface area of the dispensed hydrogel, thereby drawing up excess sheath fluid from the receiving surface and optionally from a surface of the dispensed hydrogel, thereby eliminating pooling of sheath fluid on the receiving surface and/or the dispensed hydrogel.

In one embodiment, the one or more vacuum tubes are provided, at least in part, in one or more extensions projecting from the print head, the extensions projecting in the same general direction as the extension comprising the print head orifice and dispensing channel (see, for example, FIG. 10). In such embodiments, the one or more extensions comprising vacuum tubes do not extend further than the extension comprising the print head orifice and dispensing channel so as not to interfere with dispensed and deposited hydrogel.

It is contemplated that in some embodiments, the fluid removal feature may be a feature of the sheath fluid composition itself. For example, the sheath fluid composition may be designed to evaporate after it is dispensed from the print head orifice, thereby eliminating pooling of excess sheath fluid on the receiving surface or on surfaces of dispensed hydrogel. For example, the sheath fluid may have a boiling point that results in evaporation after being dispensed, while remaining in a liquid state prior to being dispensed.

Method of Printing a Three Dimensional Structure

In an aspect, a method of printing a three-dimensional (3D) structure is provided.

The method first comprises providing a design for a 3D structure to be printed. The design may be created using commercially available CAD software. In one embodiment, the design comprises information regarding specific materials (e.g., for heterogeneous structures comprising multiple materials) to be assigned to specific geometrical locations in the design.

The method comprises the use of a 3D printer, the printer comprising: a print head, a receiving surface for receiving material dispensed by the print head; and a positioning unit operably coupled to the receiving surface, the positioning unit for positioning the print head at a location in three dimensional space above the receiving surface. For example, various embodiments of the printing system provided herein may be used in the method of printing a 3D structure.

The method comprises providing at least two materials to be dispensed by the print head, such as a sheath fluid and a hydrogel fluid. In preferred embodiments, one or more cell types are compatible with, and optionally dispensed within, the hydrogel. In a preferred embodiment, the sheath fluid serves as a lubricating agent for lubricating movement of the hydrogel within and from the print head. In a preferred embodiment, the sheath fluid comprises a cross-linking agent for solidifying at least a portion of the hydrogel before or while it is dispensed from the print head.

The method comprises communicating the design to the 3D printer. Communication can be achieved, for example, by a programmable control processor.

The method comprises controlling relative positioning of the print head and the receiving surface in three dimensional space and simultaneously dispensing from the print head the sheath fluid and the hydrogel, alone or in combination. In preferred embodiments, the materials dispensed from the print ahead are dispensed coaxially, such that the sheath fluid envelopes the hydrogel. Such coaxial arrangement allows the cross-linking agent to solidify the hydrogel, thereby resulting in a solid hydrogel fiber, which is dispensed from the printer head.

The method comprises depositing a first layer of the dispensed materials on the receiving surface, the first layer comprising an arrangement of the material specified by the design and iteratively repeating the depositing step, depositing subsequent material onto the first and subsequent layers of material, thereby depositing layer upon layer of dispensed materials in a geometric arrangement specified by the design to produce the cell-laden 3D structure.

In preferred embodiments, a plurality of materials, for example multiple hydrogels, at least some of which comprise one or more cell types, are deposited in a controlled sequence, thereby allowing a controlled arrangement of hydrogels and cell types to be deposited in a geometric arrangement specified by the design.

In preferred embodiments, the method comprises removing excess sheath fluid from the receiving surface and optionally from the surface of the dispensed hydrogel. For example, the step of removing the excess sheath fluid can be done continuously throughout the printing process, thereby removing excess fluid that may otherwise interfere with layering the dispensed materials in the geometric arrangement provided by the design. Alternatively, the step of removing excess sheath fluid may be done intermittently throughout the printing process in sequence with or simultaneously with one or more depositing steps. In some embodiments, removal of excess sheath fluid is achieved by drawing the fluid off of the receiving surface and optionally off of a surface of the dispensed hydrogel. In another embodiment removal of excess sheath fluid is achieved by drawing excess fluid through the receiving surface, the receiving surface comprising pores sized to allow passage of the sheath fluid. In another embodiment removal of excess sheath fluid is achieved by providing a sheath fluid that evaporates after being dispensed from the print head orifice.

Exemplary Uses of Embodiments of the System and Method of Printing Cell-Laden Three Dimensional Structures In some embodiments, structures generated using the system and method provided herein can be useful in the field of drug discovery, where, for example, determining cellular responses to various chemical compounds and compositions are of interest. Use of 3D cell cultures fabricated using embodiments of the systems and methods provided herein may provide experimental conditions that more closely resemble in vivo cellular and tissue conditions relative to 2D cell cultures. 3D arrangement of the cells may more closely mimic in vivo cell-cell interactions and responses to external stimuli and the heterogeneous nature of the 3D structures that can be generated using the apparatus and methods provided permit study of tissues and potentially organs. It is contemplated that 3D cell-laden structures fabricated using embodiments of the systems and methods provided herein may provide a similar benefit to the cosmetics industry by offering an alternative means to testing cosmetic products.

In some embodiments, various embodiments of the system and method provided herein are compatible with standard well-plate technology. Well-plates or well-plate inserts may be used with or as part of the print bed in the methods and systems provided herein. Various embodiments of the system and method provided herein are thus compatible with instruments and practices that utilize well-plates, allowing them to be readily integrated into existing process streams.

In some embodiments, the microfluidic channels within the print head are compatible with other microfluidic modules. For example, known microfluidic modules may be included in the print head of the systems provided herein upstream of the print head orifice. Such modules may include, for example, cell counting, cell sorting, cell analyzing, and/or concentration gradient generating modules.

In some embodiments, throughput of 3D printing may be increased by adding to the system additional print heads in parallel. Each print head comprising all of the elements required to print a multi-material structure, thus allowing several 3D structures to be printed simultaneously by including additional print heads in the system.

Although the invention has been described with reference to certain specific embodiments, various modifications thereof will be apparent to those skilled in the art without departing from the purpose and scope of the invention as outlined in the claims appended hereto. Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The disclosures of all prior art recited herein are incorporated herein by reference as if set forth in their entirety.

REFERENCES

The following references are provided as examples of the known art relating to the present invention. The following listing is not intended to comprise a comprehensive list of all relevant art. The entire contents of all references listed in the present specification, including the following documents, are incorporated herein by reference as if set forth in their entirety.

1. Su-Jung Shin, Ji-Young Park, Jin-Young Lee, Ho Park, Yong-Doo Park, Kyu-Back Lee, Chang-Mo Whang, and Sang-Hoon Lee, ""On the fly" continuous generation of alginate fibers using a microfluidic device", Langmuir, Vol. 23, 2007, pp. 9104-9108.
2. Saif Khalil, and Wei Sun, "Bioprinting endothelial cells with alginate for 3D tissue constructs", Journal of Biomechanical Engineering, Vol. 131, 2009, pp. 111002-1-111002-8.
3. Min Hu, Rensheng Deng, Karl M. Schumacher, Motoichi Kurisawa, Hongye Ye, Kristy Purnamawati, and Jackie Y. Ying, "Hydrodynamic spinning of hydrogel fibers", Biomaterials, Vol. 31, 2010, pp. 863-869.
4. Byung Kim, Intae Kim, Wooseok Choi, Sun Won Kim, JooSung Kim, and Geunbae Lim, "Fabrication of cell-encapsulated alginate microfiber scaffold using microfluidic channel", Journal of Manufacturing Science and Engineering, Vol. 130, 2008, pp. 021016-1-021016-6.
5. Edward Kang, Su-Jung Shin, Kwang Ho Lee, and Sang-Hoon Lee, "Novel PDMS cylindrical channels that generate coaxial flow, and application to fabrication of microfibers and particles", Lab on a Chip, Vol. 10, 2010, pp. 1856-1861.
6. Hiroaki Onoe, Riho Gojo, Yukiko Tsuda, Daisuke Kiriyaand, and Shoji Takeuchi, "Core-shell gel wires for the construction of large area heterogeneous structures with biomaterials", IEEE MEMS Conference, 2010, pp. 248-251.
7 Setareh Ghorbanian (2010), Microfluidic probe for direct write of soft cell scaffolds, M. Eng. Thesis. McGill University: Canada.
8. Edward Kang, Gi Seok Jeong, Yoon Young Choi, Kwang Ho Lee, Ali Khademhosseini, and Sang-Hoon Lee, "Digitally tunable physicochemical coding of material composition and topography in continuous microfibers", Nature Materials, Vol. 10, 2011, pp. 877-883.
9. EP 2489779 A1
10. US 2006/0105011 A1
11. US 2011/0136162 A1
12. US 2012/0089238 A1
13. WO 2012009363 A1

We claim:

1. A system for additive manufacturing of three-dimensional structures, the system comprising:
  at least one print head for receiving and dispensing at least one first material and at least one second material, the print head comprising:
    an orifice for dispensing the materials and at least two inlets for receiving materials in fluid communication with respective microfluidic channels arranged within the print head, the microfluidic channels comprising two first channels for receiving and directing the at least one first material, two second channels for receiving and directing the at least one second material, and a third channel joining together with each of the first channels at a first intersection point to form a dispensing channel which extends to the orifice, the two second channels intersecting at a second intersection point and joining together to form the third channel which extends to the first intersection point;
    wherein the third channel has a diameter less than each of the first channels and the dispensing channel, whereby flow of the at least one first material from the first channels forms a coaxial sheath around the at least one second material in the dispensing channel upon printing;
  a receiving surface for receiving a first layer of the materials dispensed from the orifice, wherein the receiving surface comprises a porous membrane comprising pores sized to permit passage of excess first material there through;
  a fluid removal feature for removing excess first material dispensed from the orifice, wherein the fluid removal feature comprises an absorbent material or a vacuum for drawing the excess first material away from or through the receiving surface;
  a positioning unit for positioning the orifice of the print head in three dimensional space, the positioning unit operably coupled to the print head; and
  a dispensing means for dispensing the materials from the orifice of the print head.

2. The system of claim 1, further comprising a programmable control processor for controlling the positioning unit and for controlling dispensing of the materials from the print head onto the receiving surface.

3. The system of claim 1, further comprising reservoirs for containing the materials, the reservoirs being fluidly coupled respectively to the microfluidic channels in the print head.

4. The system of claim 1, wherein the print head further comprises a hollow projection configured to extend from the orifice toward the receiving surface.

5. The system of claim 1, further comprising fluidic switches, each fluidic switch corresponding to one of the microfluidic channels in the print head and configured to allow or disallow fluid flow in the microfluidic channels of the print head when actuated.

6. The system of claim 5, wherein the fluidic switches comprise valves.

7. The system of claim 1, wherein the dispensing means comprises a pressure control unit.

8. The system of claim 1, wherein the at least one first material comprises a sheath fluid and the at least one second material comprises at least one hydrogel.

9. The system of claim 1, wherein the two second channels comprise two hydrogel channels each being adapted to convey respective hydrogels.

10. The system of claim 9, wherein the two hydrogel channels comprise a core channel for receiving and directing a hydrogel core material and a shell channel for receiving and directing a hydrogel shell material; wherein the shell channel and the third channel have larger diameters than the core channel to facilitate coaxial focusing of the hydrogel core and hydrogel shell materials, whereby flow of the hydrogel shell material from the shell channel forms a coaxial sheath around the hydrogel core material in the third channel.

11. The system of claim 1, wherein the at least one first material comprises a cross-linking agent for solidifying the at least one second material upon contact therewith at the first intersection point and/or in the dispensing channel.

12. The system of claim 1, wherein the at least one second material comprises living cells.

13. The system of claim 1, wherein each of the first channels is configured to flank the third channel at the first intersection point.

14. A method of printing a three-dimensional (3D) structure, the method comprising:
  providing a system for additive manufacturing of three-dimensional structures according to claim 1;
  providing the materials to be dispensed, the materials to be dispensed comprising a sheath fluid and one or more hydrogels;
  encoding the system with a 3D structure to be printed;

dispensing from the print head orifice the materials to be dispensed, wherein the sheath fluid and the one or more hydrogels are dispensed in a coaxial arrangement, and wherein the sheath fluid envelops the one or more hydrogels;

depositing a first layer of the dispensed materials on the receiving surface;

repeating the depositing step by depositing subsequent dispensed materials on the first and any subsequent layers of deposited materials, thereby depositing layer upon layer of dispensed materials in a geometric arrangement according to the 3D structure; and removing excess sheath fluid dispensed by the printhead orifice at one or more time point during or between depositing steps.

15. The method of claim 14, wherein the sheath fluid comprises a cross-linking agent suitable for cross-linking and solidifying at least one of the one or more hydrogels upon contact therewith, the contact creating a hydrogel fiber.

16. The method of claim 14, wherein the two second channels comprise two hydrogel channels each being adapted to convey respective hydrogels and the materials to be dispensed comprise a hydrogel core material, a hydrogel shell material, and a sheath fluid, wherein the two hydrogel channels comprise a core channel for receiving and directing the hydrogel core material and a shell channel for receiving and directing the hydrogel shell material, wherein the shell channel and the third channel have larger diameters than the core channel to facilitate coaxial focusing of the hydrogel core and hydrogel shell materials, whereby flow of the hydrogel shell material from the shell channel forms a coaxial sheath around the hydrogel core material in the third channel, wherein the hydrogel shell material envelops the hydrogel core material, and wherein the sheath fluid envelops the hydrogel shell material.

17. The method of claim 16, wherein the sheath fluid comprises a cross-linking agent suitable for cross-linking and solidifying the hydrogel shell material, optionally suitable for cross-linking and solidifying the hydrogel core material, upon contact therewith, the contact creating a hydrogel fiber.

18. The method of claim 17, wherein the hydrogel core material is incapable of gelling upon contact with the cross-linking agent, thereby facilitating creating of a hollow hydrogel fiber.

19. The method of claim 16, wherein the hydrogel core material solidifies following deposition.

20. The method of claim 14, wherein the depositing step and the removing step are carried out continuously, thereby continuously removing the excess sheath fluid as the layers of dispensed materials are deposited.

21. The method of claim 14, wherein the removing step is carried out intermittently between and/or at the same time as the depositing step, thereby intermittently removing the excess sheath fluid as the layers of dispensed materials are deposited.

22. The method of claim 14, wherein at least one of the one or more hydrogels are adapted for supporting growth and/or proliferation of living cells dispersed therein.

\* \* \* \* \*